(12) United States Patent
Gabbay

(10) Patent No.: US 9,005,279 B2
(45) Date of Patent: Apr. 14, 2015

(54) BEATING HEART BUTTRESS AND IMPLANTATION METHOD TO PREVENT PROLAPSE OF A HEART VALVE

(76) Inventor: Shlomo Gabbay, New York, NY (US)

(*) Notice: Subject to any disclaimer, the term of this patent is extended or adjusted under 35 U.S.C. 154(b) by 128 days.

(21) Appl. No.: 13/294,453

(22) Filed: Nov. 11, 2011

(65) Prior Publication Data
US 2012/0150290 A1 Jun. 14, 2012

Related U.S. Application Data

(60) Provisional application No. 61/413,103, filed on Nov. 12, 2010.

(51) Int. Cl.
*A61F 2/24* (2006.01)
(52) U.S. Cl.
CPC ..................... *A61F 2/2454* (2013.01)
(58) Field of Classification Search
CPC .............................. A61F 2/2448; A61F 2/2403
USPC ........................................ 623/2.11, 2.36–2.37
See application file for complete search history.

(56) References Cited

U.S. PATENT DOCUMENTS

| | | | |
|---|---|---|---|
| 4,042,979 A | 8/1977 | Angell | |
| 4,084,268 A | 4/1978 | Ionescu et al. | |
| 4,218,783 A * | 8/1980 | Reul et al. | 623/2.17 |
| 4,240,161 A | 12/1980 | Huffstutler et al. | |
| 4,350,492 A | 9/1982 | Wright et al. | |
| 4,477,930 A | 10/1984 | Totten et al. | |
| 4,491,986 A | 1/1985 | Gabbay | |
| 4,725,274 A | 2/1988 | Lane et al. | |
| 4,759,758 A | 7/1988 | Gabbay | |
| 5,258,021 A | 11/1993 | Duran | |
| 5,411,552 A | 5/1995 | Anderson et al. | |
| 5,500,014 A | 3/1996 | Quijano et al. | |
| 5,549,665 A | 8/1996 | Vesely et al. | |
| 5,554,185 A | 9/1996 | Block et al. | |
| 5,584,879 A | 12/1996 | Reimold et al. | |
| 5,669,919 A * | 9/1997 | Sanders et al. | 606/148 |
| 5,800,527 A | 9/1998 | Jansen et al. | |
| 5,840,081 A | 11/1998 | Andersen et al. | |
| 5,855,601 A | 1/1999 | Bessler et al. | |
| 5,855,602 A | 1/1999 | Angell | |
| 5,861,028 A | 1/1999 | Angell | |
| 5,948,017 A | 9/1999 | Taheri | |
| 6,168,614 B1 | 1/2001 | Andersen et al. | |
| 6,419,695 B1 * | 7/2002 | Gabbay | 623/2.36 |
| 6,869,444 B2 | 3/2005 | Gabbay | |
| 7,160,322 B2 | 1/2007 | Gabbay | |
| 7,404,824 B1 * | 7/2008 | Webler et al. | 623/2.36 |
| 7,510,573 B2 | 3/2009 | Gabbay | |
| 7,635,386 B1 * | 12/2009 | Gammie | 623/2.11 |
| 7,722,666 B2 * | 5/2010 | Lafontaine | 623/2.11 |

(Continued)

FOREIGN PATENT DOCUMENTS

| | | |
|---|---|---|
| EP | 0850607 | 7/1998 |
| WO | WO 92/13502 | 8/1992 |

*Primary Examiner* — Thomas J Sweet
*Assistant Examiner* — Seema Mathew
(74) *Attorney, Agent, or Firm* — Tarolli, Sundheim, Covell & Tummino LLP

(57) ABSTRACT

An apparatus and method for mitigating prolapsed are disclosed. The apparatus includes a contact member and an elongated rod that can be used to hold the contact member in position for coapting with a patient's native leaflets. A similarly configured sizing apparatus can also be used to facilitate implantation.

17 Claims, 14 Drawing Sheets

(56) References Cited

U.S. PATENT DOCUMENTS

| | | | |
|---|---|---|---|
| 8,252,051 B2* | 8/2012 | Chau et al. | 623/2.12 |
| 2003/0083742 A1* | 5/2003 | Spence et al. | 623/2.16 |
| 2003/0199975 A1* | 10/2003 | Gabbay | 623/2.36 |
| 2005/0038508 A1* | 2/2005 | Gabbay | 623/2.36 |
| 2005/0283232 A1* | 12/2005 | Gabbay | 623/2.11 |
| 2006/0142848 A1* | 6/2006 | Gabbay | 623/1.26 |
| 2006/0195183 A1* | 8/2006 | Navia et al. | 623/2.18 |
| 2006/0241748 A1* | 10/2006 | Lee et al. | 623/2.37 |
| 2006/0259135 A1* | 11/2006 | Navia et al. | 623/2.11 |
| 2007/0005134 A1* | 1/2007 | McCarthy | 623/2.17 |
| 2007/0255399 A1* | 11/2007 | Eliasen et al. | 623/2.36 |
| 2007/0282429 A1* | 12/2007 | Hauser et al. | 623/1.16 |
| 2008/0097595 A1* | 4/2008 | Gabbay | 623/2.42 |
| 2008/0288060 A1* | 11/2008 | Kaye et al. | 623/2.36 |
| 2010/0063586 A1* | 3/2010 | Hasenkam et al. | 623/2.37 |
| 2010/0262233 A1* | 10/2010 | He | 623/2.36 |
| 2011/0106247 A1* | 5/2011 | Miller et al. | 623/2.17 |
| 2012/0022640 A1* | 1/2012 | Gross et al. | 623/2.11 |
| 2012/0029628 A1* | 2/2012 | Rowe | 623/2.11 |
| 2012/0035712 A1* | 2/2012 | Maisano et al. | 623/1.26 |
| 2012/0035713 A1* | 2/2012 | Lutter et al. | 623/1.26 |
| 2012/0101571 A1* | 4/2012 | Thambar et al. | 623/2.17 |
| 2013/0079873 A1* | 3/2013 | Migliazza et al. | 623/2.17 |
| 2013/0166022 A1* | 6/2013 | Conklin | 623/2.17 |
| 2013/0197632 A1* | 8/2013 | Kovach et al. | 623/2.37 |
| 2013/0289717 A1* | 10/2013 | Solem | 623/2.11 |
| 2014/0025163 A1* | 1/2014 | Padala et al. | 623/2.18 |
| 2014/0031928 A1* | 1/2014 | Murphy et al. | 623/2.18 |
| 2014/0107773 A1* | 4/2014 | Huber | 623/2.18 |
| 2014/0214160 A1* | 7/2014 | Naor | 623/2.36 |
| 2014/0236291 A1* | 8/2014 | Schweich et al. | 623/2.36 |
| 2014/0249621 A1* | 9/2014 | Eidenschink | 623/2.11 |
| 2014/0324164 A1* | 10/2014 | Gross et al. | 623/2.37 |

* cited by examiner

BEATING HEART BUTTRESS AND IMPLANTATION METHOD TO PREVENT PROLAPSE OF A HEART VALVE

RELATED APPLICATION

This application claims the benefit of U.S. Provisional Application No. 61/413,103 filed Nov. 12, 2010, and entitled BEATING HEART BUTTRESS AND IMPLANTATION METHOD TO PREVENT PROLAPSE OF A HEART VALVE, which is incorporated herein by reference in its entirety.

TECHNICAL FIELD

The invention relates generally to an apparatus to facilitate coaptation for a malfunctioning heart valve and a method for implanting the apparatus, such as at a mitral or an aortic position.

BACKGROUND

A heart valve may become defective or damaged, such as resulting from congenital malformation, disease, or aging. When the valve becomes defective or damaged, the leaflets may not function properly. One common problem associated with a degenerating heart valve is an enlargement of the valve annulus (e.g., dilation). Other problems that may result in valve dysfunction are chordal elongation and lesions developing on one or more of the leaflets.

DESCRIPTION

In order to provide an understanding of the concepts of various embodiments of the invention, this application includes an Appendix A, which is incorporated herein in its entirety. This Appendix comprises informal drawings of FIGS. 1-30 that includes notes and comments are written on the various FIGS. 1 through 30. The comments and notes are intended to provide a further understanding of various embodiments in the context of the examples and embodiments being shown. The following description provides these and other information and features relating to some of the FIGS. 1-30 that was not presented on the figures themselves. The comments on the figures and the following description are to be considered collectively in understanding information about various embodiments of the apparatus and methods shown and described herein.

FIGS. 1-12 depict an example of a buttress having an elongated rod extending from a central extension of the buttress. The elongated rod can be of a flexible tubular length of material that can be used to anchor the support member and buttress at the annulus in a desired position. A device can be implanted through an apical incision in the heart, such as through trocar or other implanter such as disclosed herein. Additionally, the elongated rod of the device can be utilized to urge and advance the device through the barrel of an implanter such as a trocar to the desired position. That is, the elongated rod can be gripped by the user and pushed axially through the trocar to advance the device toward its implantation site. Once at the desired position, the proximal end of the rod can be attached and secured to the heart (e.g., at the apex of the heart) to stabilize the buttress at the desired axial and angular orientation. Excess length of the elongated rod extending outwardly from the heart can be cut and removed.

FIGS. 1 and 2 depict an example of an apparatus that includes a buttress and a ring similar to U.S. Pat. No. 6,419,695, which is incorporated herein by reference. The ring can be made of a pliant (e.g., flexible) silicon rod, which can be covered with biological tissue. Any flexible material having excellent memory or Nitinol wire may be used, as both such materials can be inserted into the barrel of an implanter to a reduced cross-sectional dimension for implantation. A ring formed of these and similar material can be easily bendable to squeeze inside the implanter (See FIG. 3). The body of the device can be made of resilient flexible material with good memory that can be introduced inside the trocar as well.

FIG. 3 shows the Mitrofix can easily squeeze inside the barrel (e.g., a trocar, catheter or other implanter). The body of the apparatus, which extends axially away from the ring can be made of resilient and flexible material that is easily deformed and compressed inside the barrel and return to its desired shape when discharged.

FIG. 4, an elongated rod is connected to the tip of the outflow end of the buttress or body of the apparatus. This attachment can be strengthened by an extension suture posterior to the tissue covering the apparatus. A guidewire can also be inserted axially through a lumen that extends through the rod and through the buttress to facilitate its implantation. During implantation, which can occur transapically, the guidewire can be introduced beforehand through a very small slot close to the connection of the silicon rod covered with pericardium to the device.

FIG. 5 depicts a side view of the device of FIG. 4 with the rod attached to the buttress apparatus. As mentioned, the Rod can flexible. The guidewire extends through the device.

FIG. 6 shows a close-up view demonstrating an example of suturing of the sleeve covering the guidewire and attached to the distal end of the device.

FIG. 7 demonstrates to annular ring, such as can be formed of silicon and covered with a biocompatible natural tissue material (e.g., pericardium, dura matter or the like) or a biocompatible synthetic material. The ring is clearly shown. Afer being discharged from the barrel of the implanter, the ring spreads open and returns to its original configuration. As it spreads, it can help stabilize the side movement of the device. The axial or up-and-down movement is stabilized by the connection of the rod to the heart, such as at the apex or other heart muscle tissue through which the device is implanted.

FIG. 8 the elongated and flexible rod has been partially inserted inside the trocar, such as just before squeezing the device inside the tip of the trocar. The guidewire is also extending, through the rod and the buttress apparatus.

FIG. 9 is a device that has been inserted into the barrel of the trocar with the and surrounding the guidewire. A small portion of the devices inflow end shows out the tip of the trocar.

FIG. 10, the device is almost pushed completely inside the trocar. The tip can of the trocar can be covered with an introducer tip, such as shown and described in U.S. patent application Ser. No. 12/886,087, which was filed Sep. 20, 2010, the entire contents of which is incorporated herein by reference. By way of example, as disclosed herein, the guidewire is introduced via the apex (see, e.g., FIG. 12).

FIG. 11 displays a device that is being ejected from the trocar and along the guidewire. Thus, during implantation, the guidewire can be advanced to a desired implantation site and the device can be urged along the guidewire.

FIG. 12 is an example of an implantation method: The device can be positioned inside the left atrium by control of 2D-echo or X-ray. The house of the device and the flexible trocar are guided over the guidewire to bring the tip beyond the mitral valve ring.

At this stage, the rod is pushed in the mitral ring when the silicon rod is slightly above the annular level. Color 2D-echo can be used to show the competence of the valve. The surgeon can position the buttress slightly up and down or right to left according to the result of the color 2D-echo, which can show if there is regurgitation or not. The echocardiographer can also measure the gradient and effective orifice area of the mitral restoration with the device when being implanted. Once the surgeon is satisfied with the position, he will tie the double purse string of the apex to stabilize the rod and device relative to the heart. The rod can be cut out and covered with a smooth biocompatible plug. The plug can further be covered with a biocompatible patch (e.g., a sheet of natural or synthetic material) that can be sutured to the apex or just covering the apex.

FIGS. 13-23B depict another example of an apparatus that can be implanted in a similar manner. This example relates to a device that can be implanted to mitigate prolapsed of anterior/posterior leaflets of a patient's heart, such as by providing a web of support that extends axially essentially as a sheet against which the respective opposing (e.g., anterior and posterior) leaflets can coapt. This device can be implanted according to a similar method to that shown and described herein with respect to the device of FIGS. 1-12.

FIG. 13 shows a device that can be made of resilient medical grade silicon with central lumen such as for catheter insertion. We see here a side view. In this example, the left side includes an elongated rod of a flexible material (e.g., silicon or other pliant material) and a central lumen extending therethrough. The lumen can be centrally located, depending on which cusp is more prolapsing. Alternatively, the middle plate can also be made of nitinol wire covered with pericardium. The contact portion (on the right side of this figure) has a shape similar to the middle plate identified as reference #20 of U.S. Pat. No. 7,160,322, which is incorporated herein by reference. It has a thinner part that becomes wider, as shown. For example, each of the side surfaces can have a configuration that is designed according to the amount of prolapsed for a given leaflet. For instance, one side can be deeper if the posterior leaflet is prolapsing more than the anterior leaflet.

FIG. 14 depicts a frontal view of the flexible rod, showing the contact surfaces. This flexible rod can be covered with a biocompatible material, such as natural or synthetic materials.

FIG. 15, by way of example, if we draw a ling going through the central lumen (axially through the rod), we see that the thickness of the contact member can be deeper than the opposite side. That is, the contact surfaces can be symmetric or non-symmetric to either side according to the need. The flexible substrate can be a pliant material, such as silicon, or it can be made of nitinol, covered with the biocompatible material.

FIG. 16 hand sketches depicting an example of the resilient rod having a central lumen and a shape that is dimension and configured for providing contact surfaces for an anterior and/ or posterior leaflet to coapt against and thereby mitigate prolapse. A central lumen can extend completely through the device as depicted in the left-side view or the lumen can extend through to another side (e.g., along one of the contact surfaces), such as can be a design consideration for different patient conditions (e.g., depending upon the amount of prolapse of a given leaflet).

FIG. 17, in this example, substrate elongated rod and the contact member are covered with a sheet of biocompatible material. The rod extends from an outflow end of the contact member. The rod can be coupled, for instance, to keep the device just above the mitral annulus when implanted, such as disclosed in FIGS. 11 & 12 the above-incorporated U.S. Pat. No. 7,160,322. The new device will be inserted from the apex (see FIGS. 23A and 23B). It can be made to be pliant enough to be squeezed inside the flexible trocar. The contact member (or buttress) can function with or without ring.

FIG. 18 shows an inflow view of the device, which includes a buttress and a ring. The elongated rod extends from the distal end of the buttress (the contact surface for opposing leaflets). The ring can help to position the buttress centrally and can also be made of flexible silicon covered with pericardium or other natural or synthetic materials. This allows better sitting on the left atrium. For instance, the ring can have a diameter wide than the buttress. The ring can also be made of nitinol wire that is covered with pericardium or other natural or synthetic materials.

Figure 11:
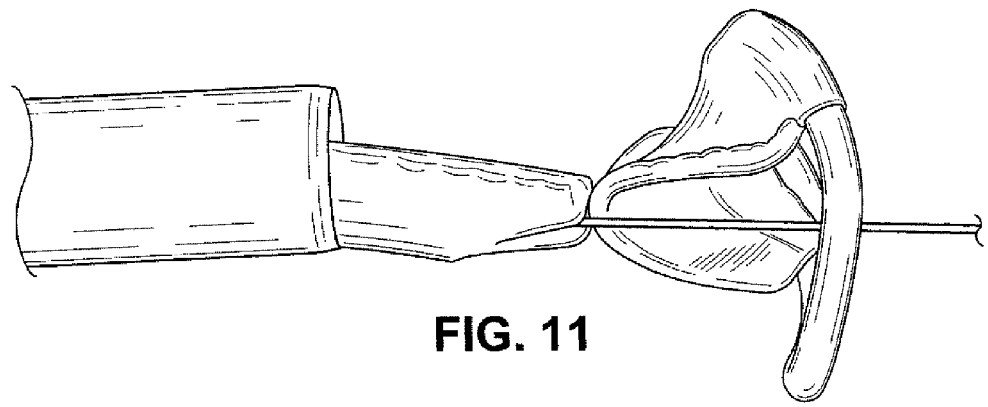
Figure 12:
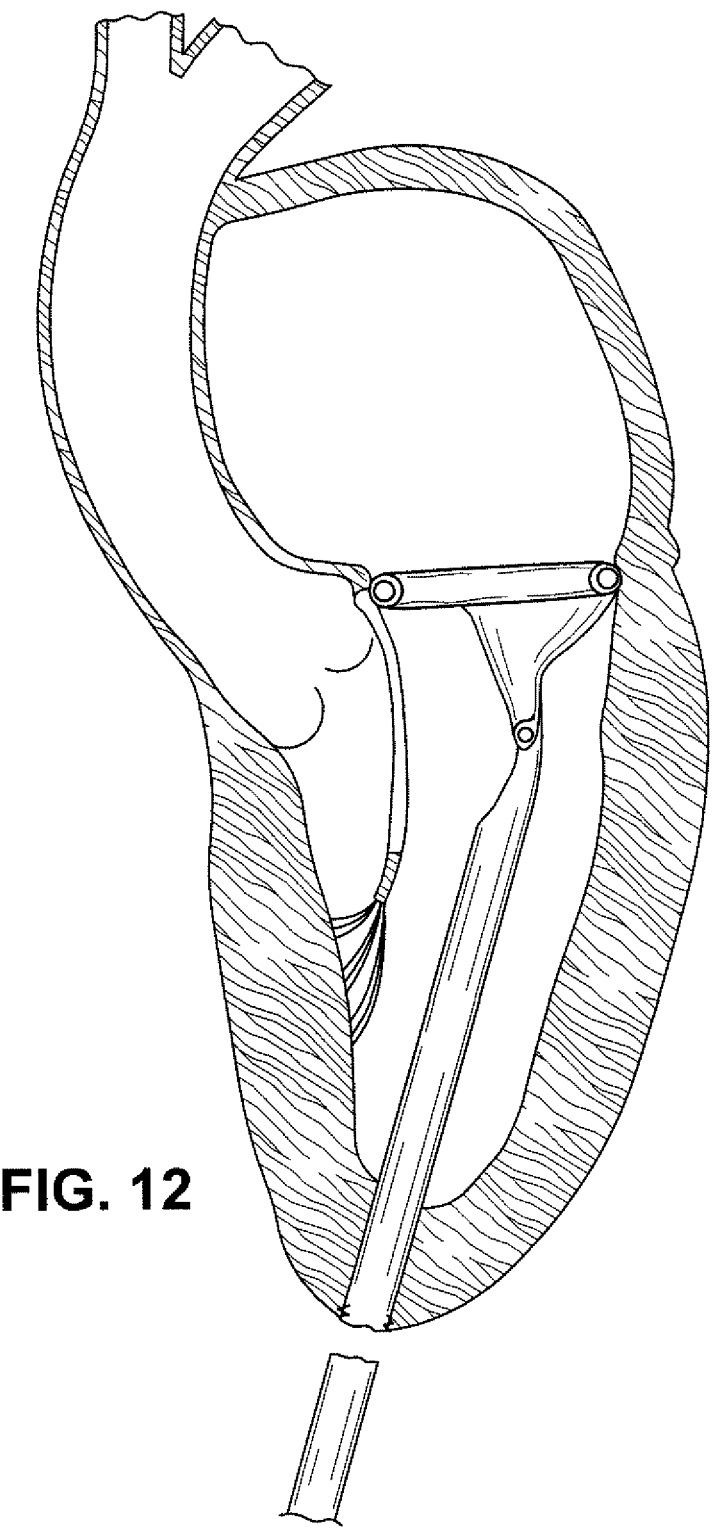
Figure 21:
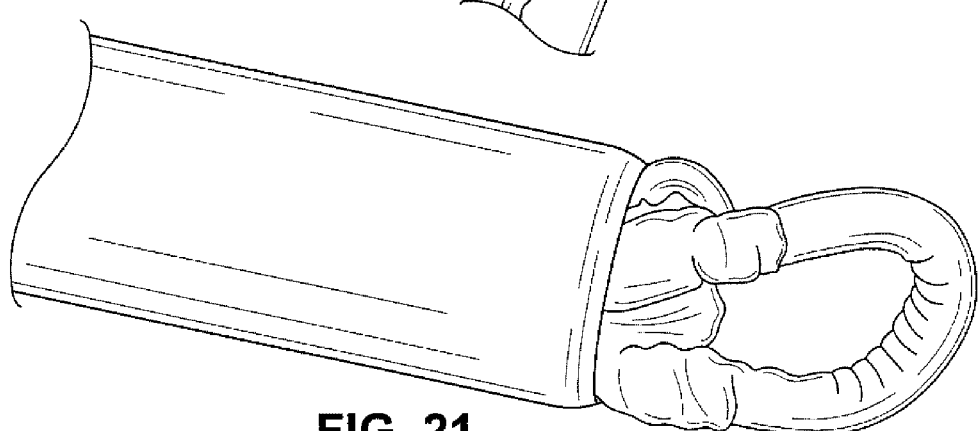

FIG. 21 demonstrates the rod, with the buttress and the ring, being introduced inside of the tip of a trocar. It is to be understood that a guidewire, which is not seen here (but see other figures herein), can be used to facilitate its implantation, such as demonstrated in FIGS. 23A and 23B. For instance, the guidewire can help slide the device and the trocar beyond the annular level of the mitral valve. The device can then be pushed out. Using 2D-echo, the surgeon can bring the device up and down or rotate left and right until the regurgitation stops completely. Once the proper position has been achieved, the surgeon can fix a proximal portion of the rod in the apex, such as by sutures. The surgeon can then remove the guidewire or catheter, cut the extra piece of the rod, and cover the tip such as described in FIG. 11 of this document.

Figure 22:
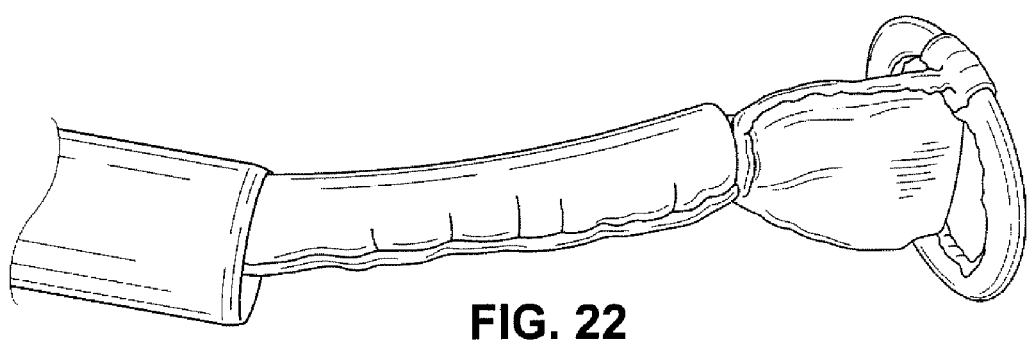

FIG. 22 the (device ring, buttress and rod) are shown being ejected from a trocar. For instance, the ejection can be performed by urging the rod (extending outwardly from a proximal end of the trocar— not shown) excess length of the rod can be cut.

Figure 23B:
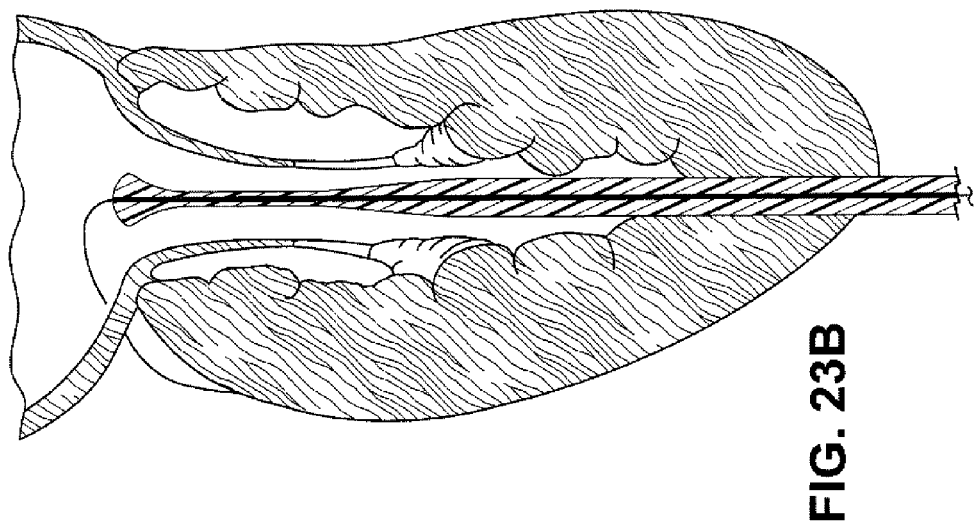
Figure 23A:
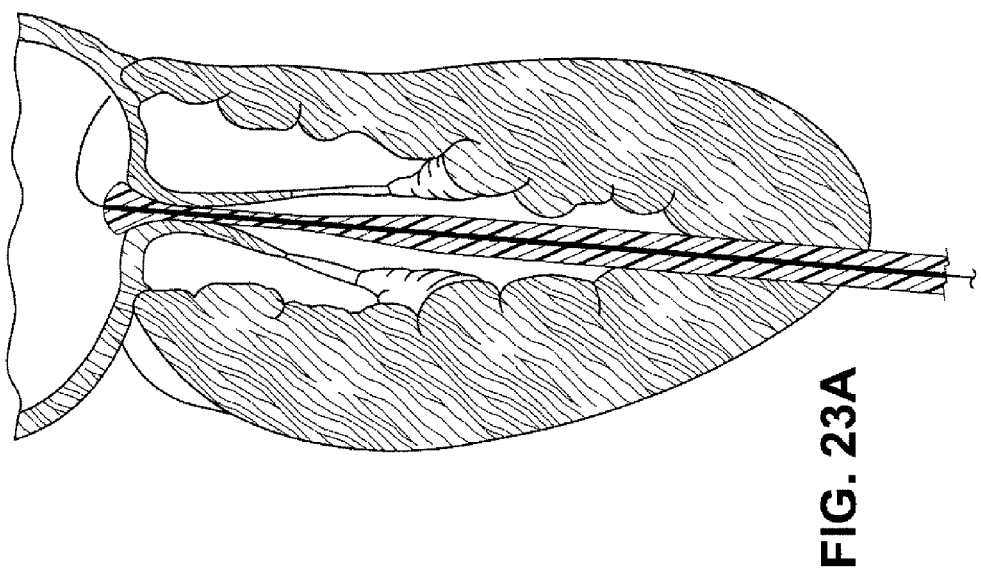

The examples of FIGS. 23A and 23B (as with respect to the examples of FIGS. 12, 28, 29 and 30) can be utilized to implant the device at the valve annulus in the absence of using sutures applied at the annulus. For example, the attachment of the rod to the heart at the apex can sufficiently stabilize the device as to maintain the orientation of the device to provide for a competent valve function.

Figure 24:
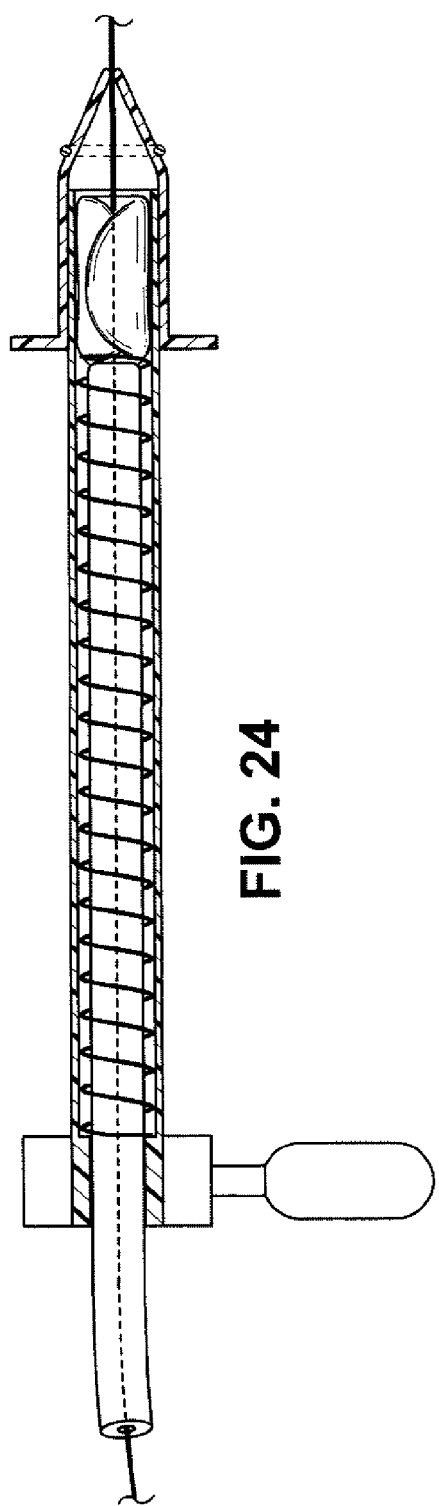

FIG. 24 depicts an example of an implanter that can be utilized for implanting the various devices (e.g., FIGS. 1-23 and 25-30) shown and described herein. As shown in this example, the buttress portion can be contained within a distal end barrel or tip portion of the implanter. The tip portion can be an introducer such as shown in the U.S. patent application Ser. No. 12/886,087, which is incorporated herein. The buttress portion can be in a larger diameter tip portion (e.g., a cage-like structure) than the part of the implanter through which the elongated rod extends. In this example, the rod extends through and beyond the proximal end of the implanter while the supporting member or buttress is contained in the tip portion. Thus, an individual can grab the free end of the rod and push it axially through the implanter for ejecting the device from the implanter and for adjusting its axial and angular position. The barrel of the implanter extending between the tip portion and the distal end can be flexible, such as by providing a spring that is mounted between a pair of circumscribing flexible side walls so that the device can be bent and curved along various paths to get to the desired implantation device, as may be needed.

As described herein, the flexible tube or rod that extends from the contact portion or buttress of the implanted device can be cut after the device is fixed at a desired implantation orientation. The distal end in which the buttress or contact members are contained can have a larger cross sectional dimension than the body that extends from there to the distal end where the handle is located. The length of the implanter should be sufficient to diverse the entire length of the heart such as for a transapical implantation shown and described herein.

FIGS. 24-30 depict an example of a buttress member that can be used for an aortic valve. The aortic buttress is needed when there is a pure dilatation of the aortic annulus (like in Marfan's Syndrome) and regurgitation with any mild annulysmal formation. The aortic buttress fixed in the apex can close the gap between the three non-coapting cusps and the regurgitation can give the patient significantly more time before he will need a big operation to fix the basic problem. Also, by solving the regurgitation problem, the natural history of the disease can be totally changed in favor of the patient.

Figure 13:
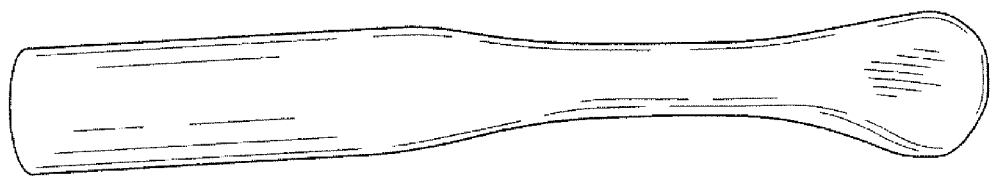
Figure 14:
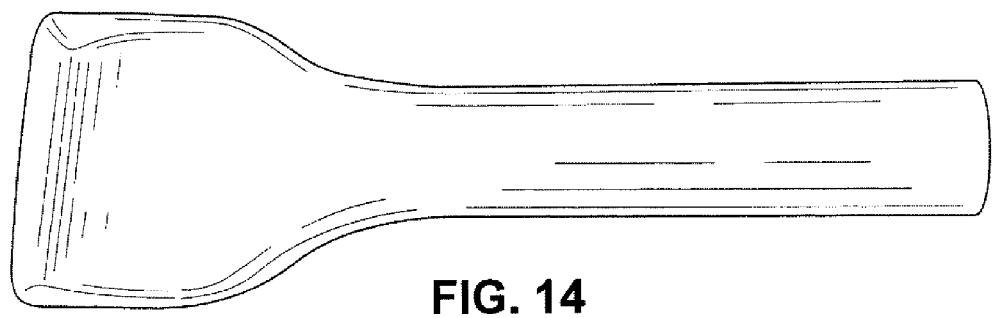
Figure 15:
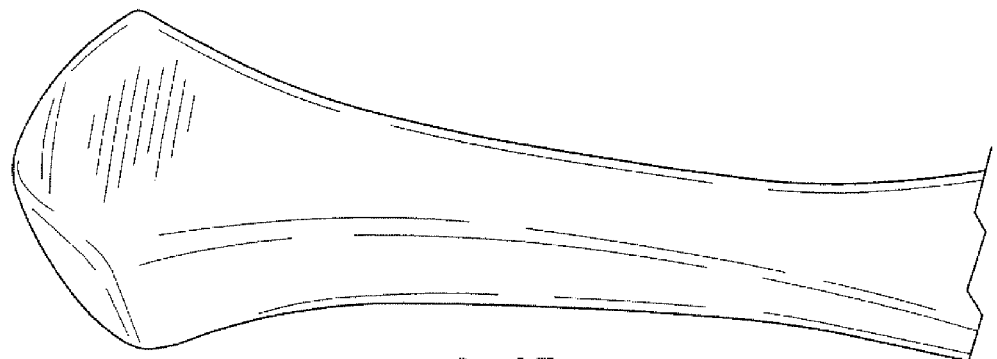
Figure 16:
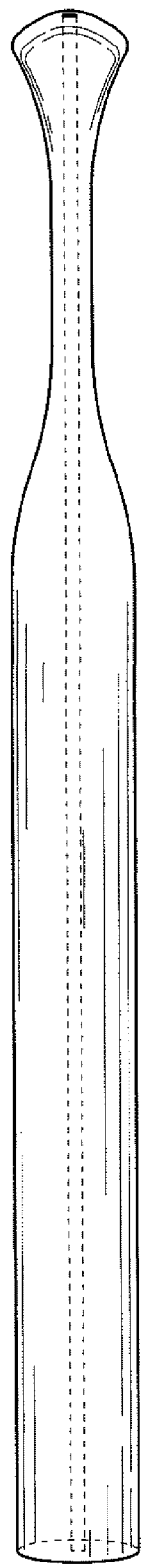
Figure 17:
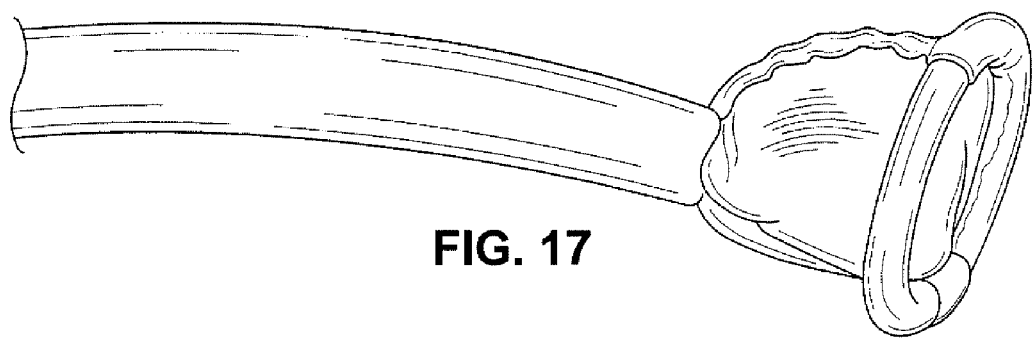
Figure 18:
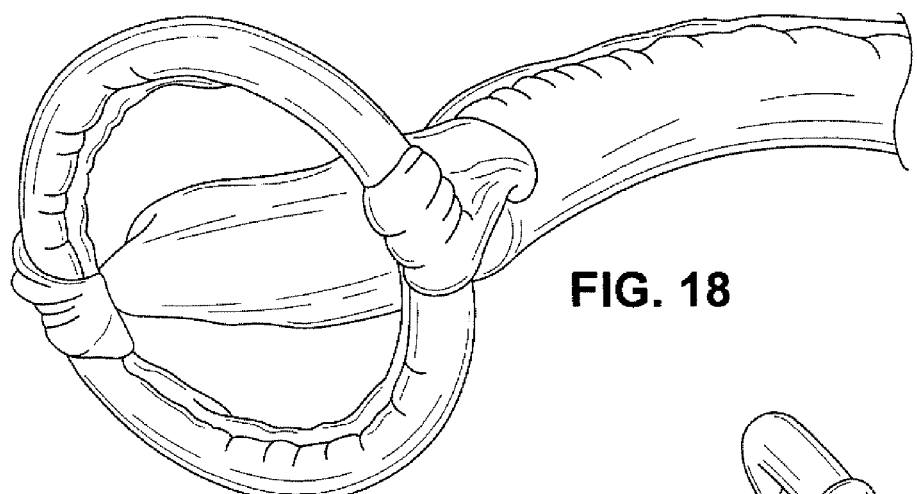
Figure 19:
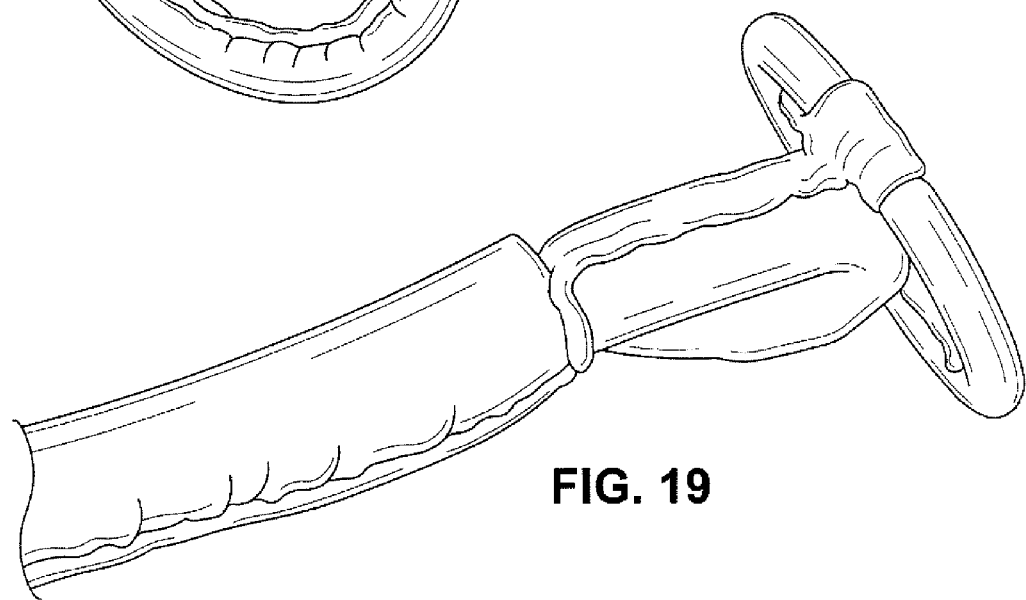
FIG. 19 shows a side view of the device from FIG. 18.
Figure 20:
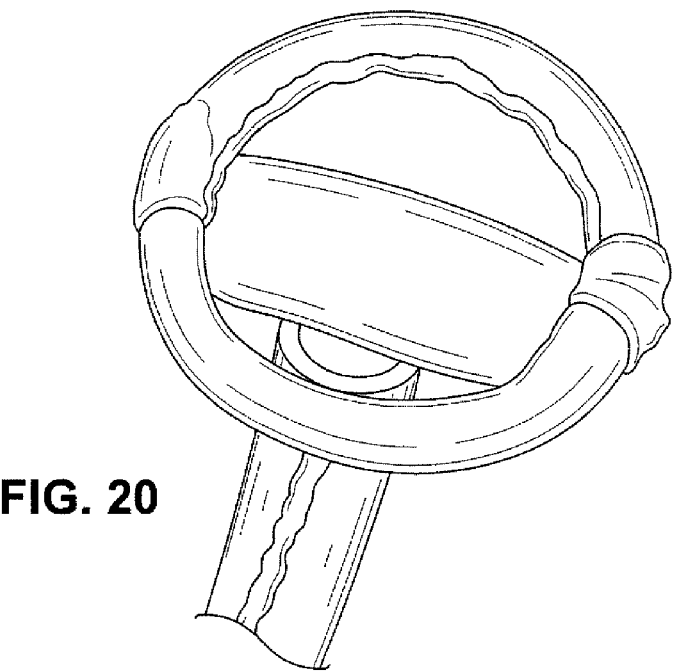
FIG. 20 shows an enlarged view of the device showing the buttress and ring.

The contacting surfaces of the buttress in the examples of FIGS. 24-30 can be similar in configuration and dimension to FIGS. 13 and 14 of U.S. Pat. No. 7,160,322, which has been incorporated herein. However, as disclosed herein the device herein can be implanted without sutures since an elongated rod (e.g., flexible tubular structure) extends from the contacting member of the device that no sutures are used. The elongated rod, similar to as explained herein, includes a lumen through which a guidewire can traverse for guiding the device to the implantation site. The buttress portion also is configured to taper down and connect to the rod at a central portion thereof (e.g., between the three buttresses). In the illustrated example, it has a lumen on it and is substantially thicker in the distal part. In order to facilitate transapical implantation, the buttress can be more tapered and rounded down as in the FIG. 28.

Figure 1:
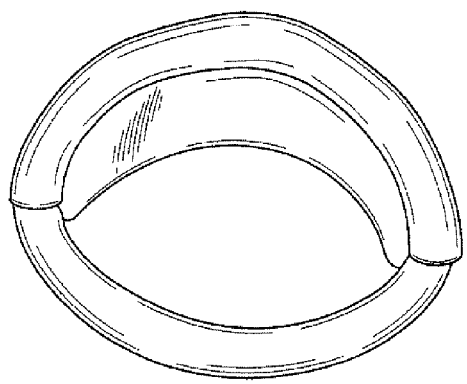
Figure 2:
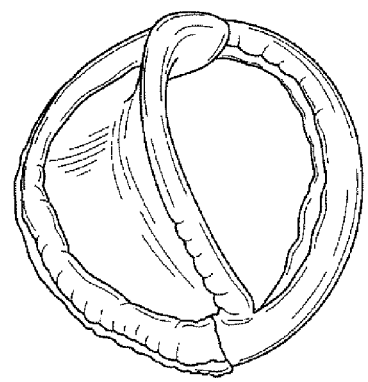
Figure 3:
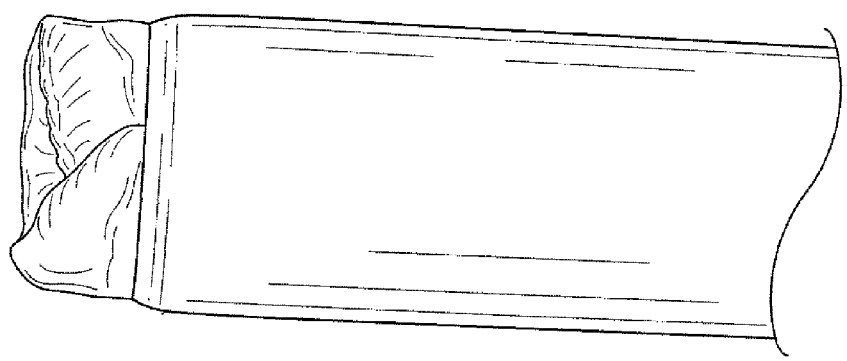
Figure 4:
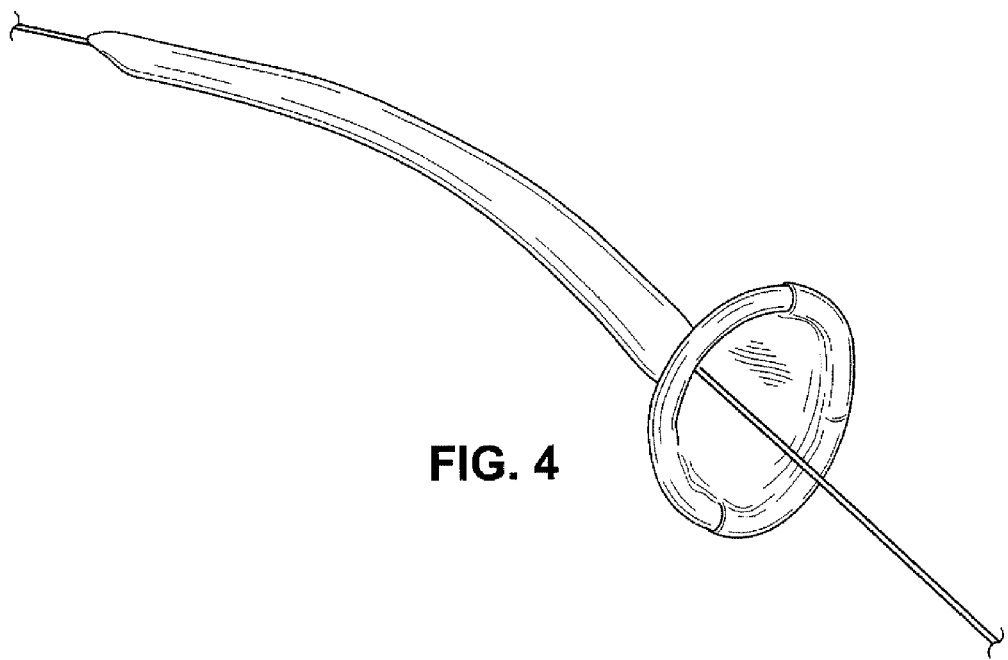
Figure 5:
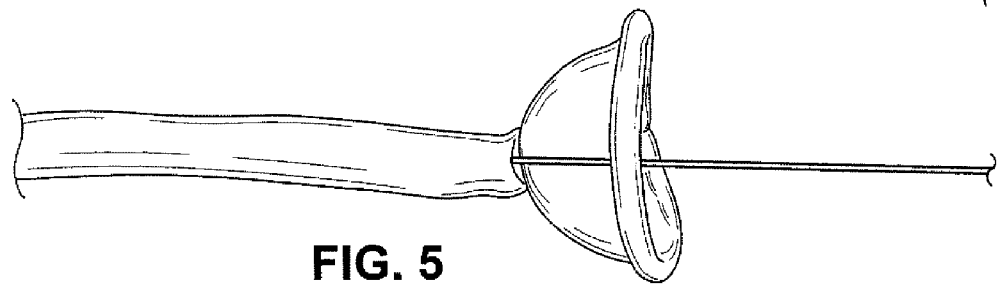
Figure 6:
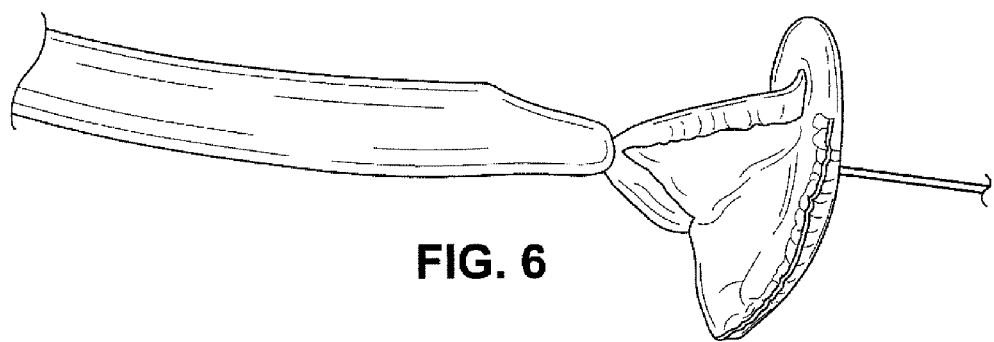
Figure 7:
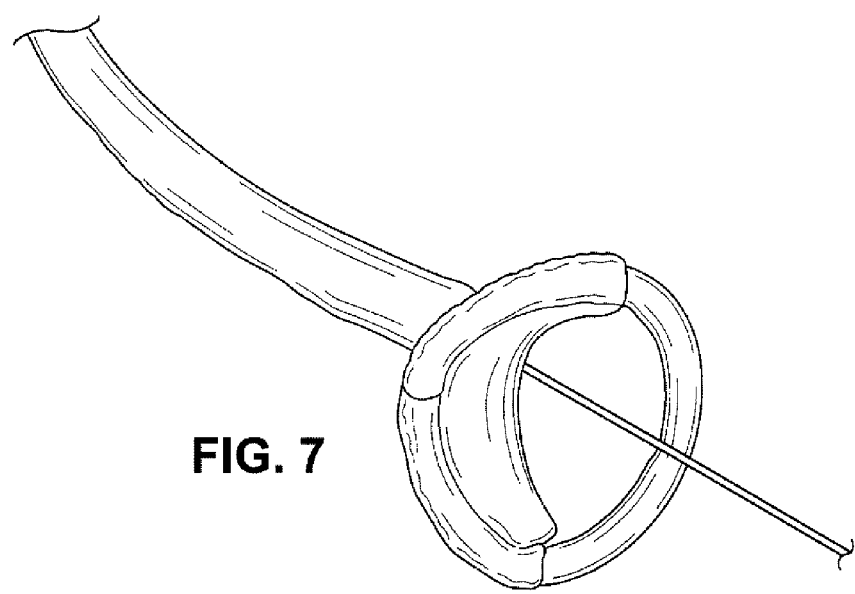
Figure 8:
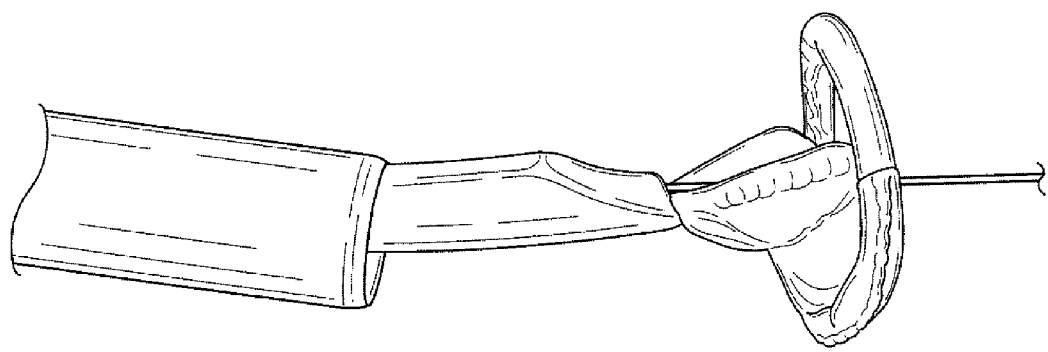
Figure 9:
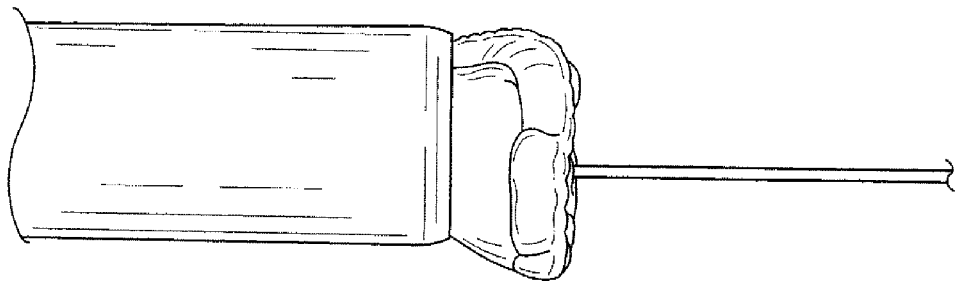
Figure 10:
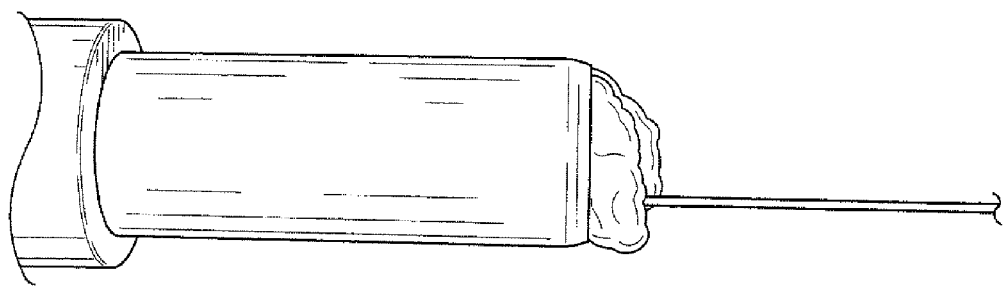
Figure 25:
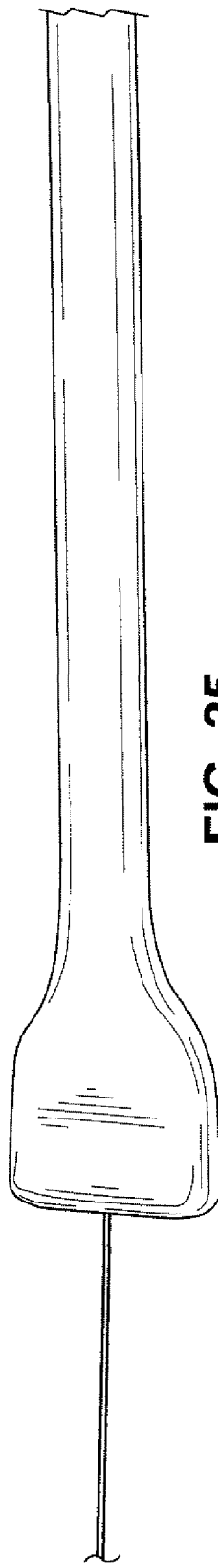
Figure 26:
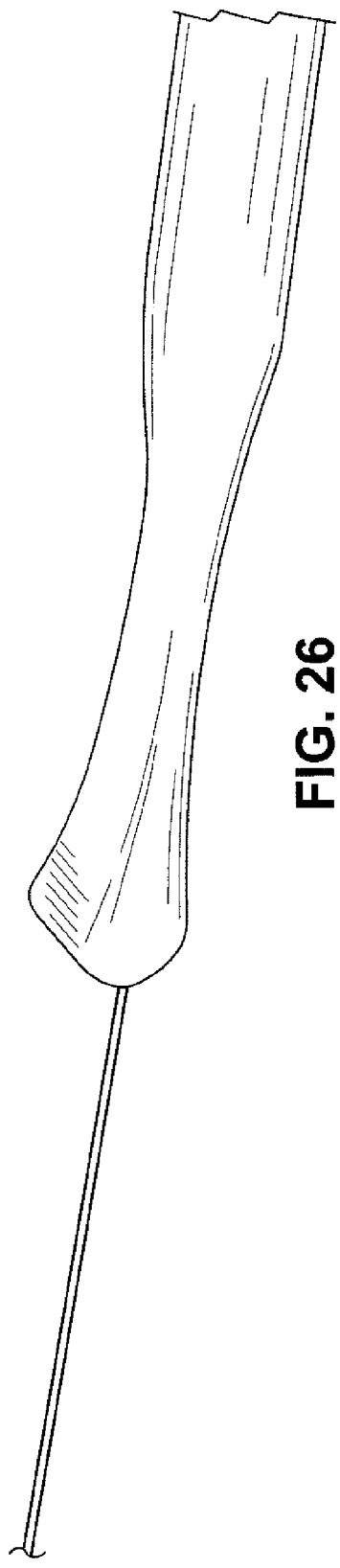
Figure 27:
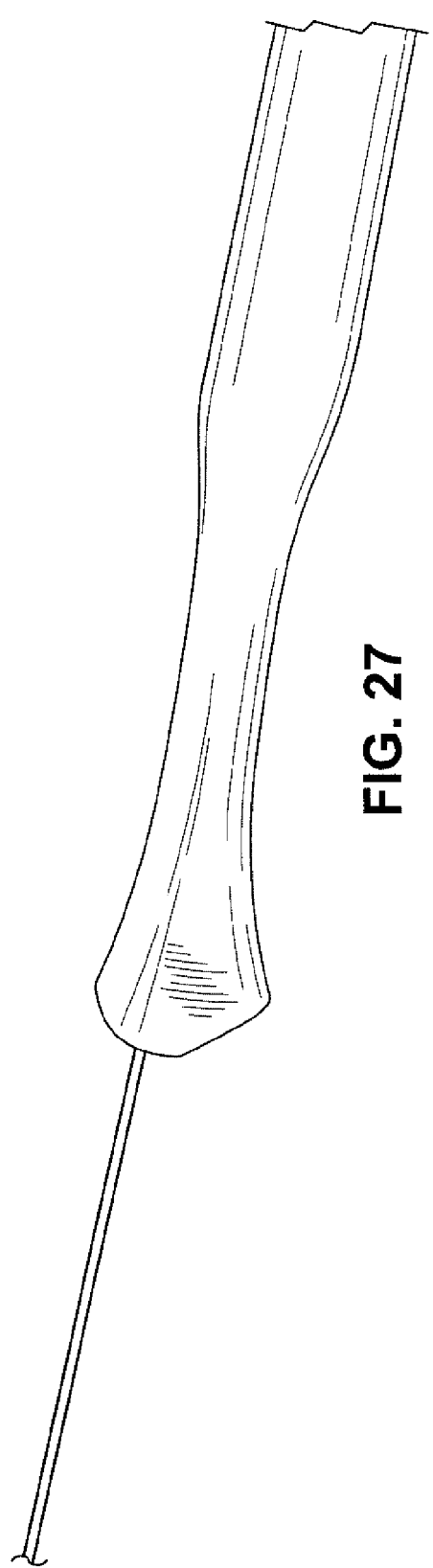
Figure 28:
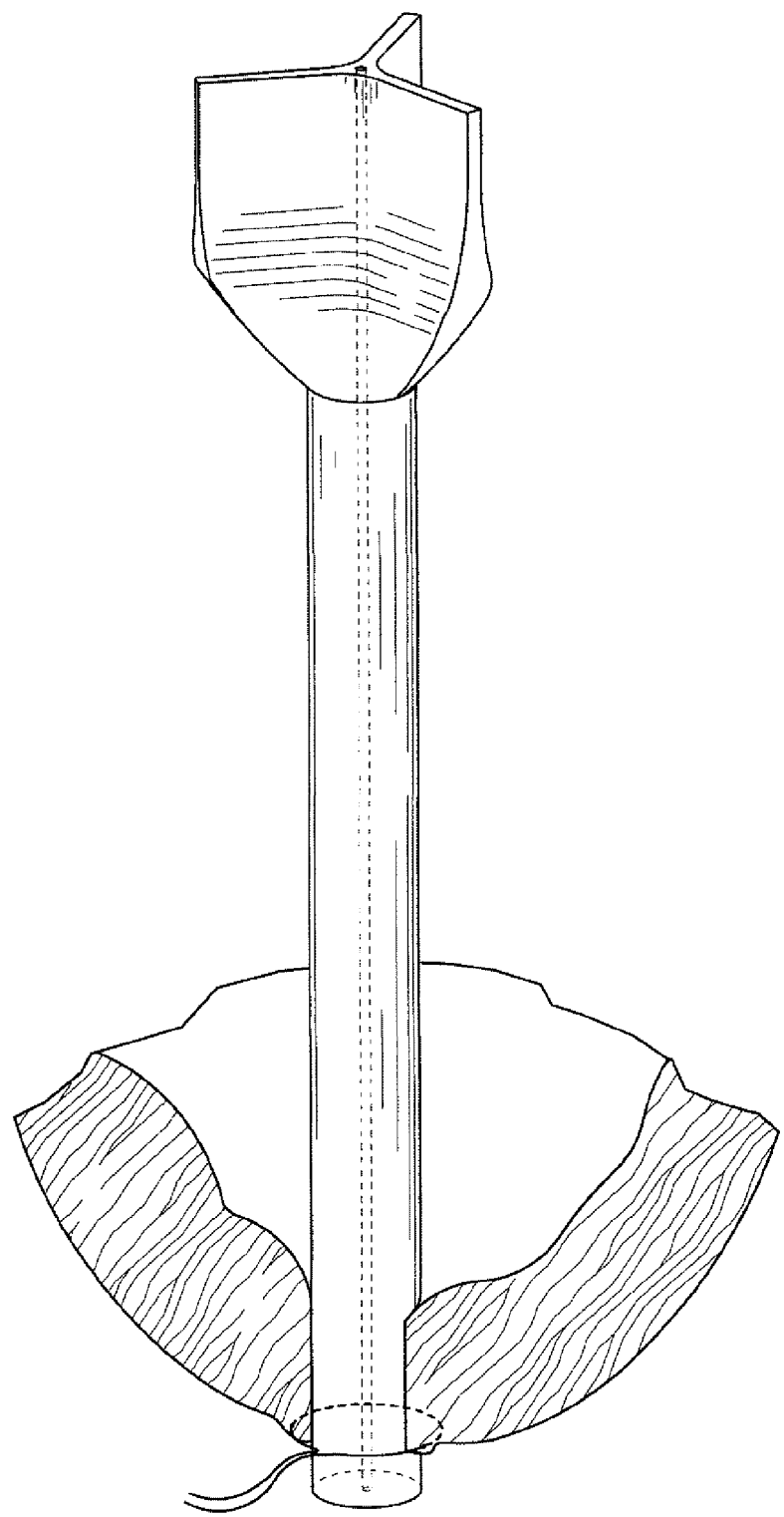
Figure 30:
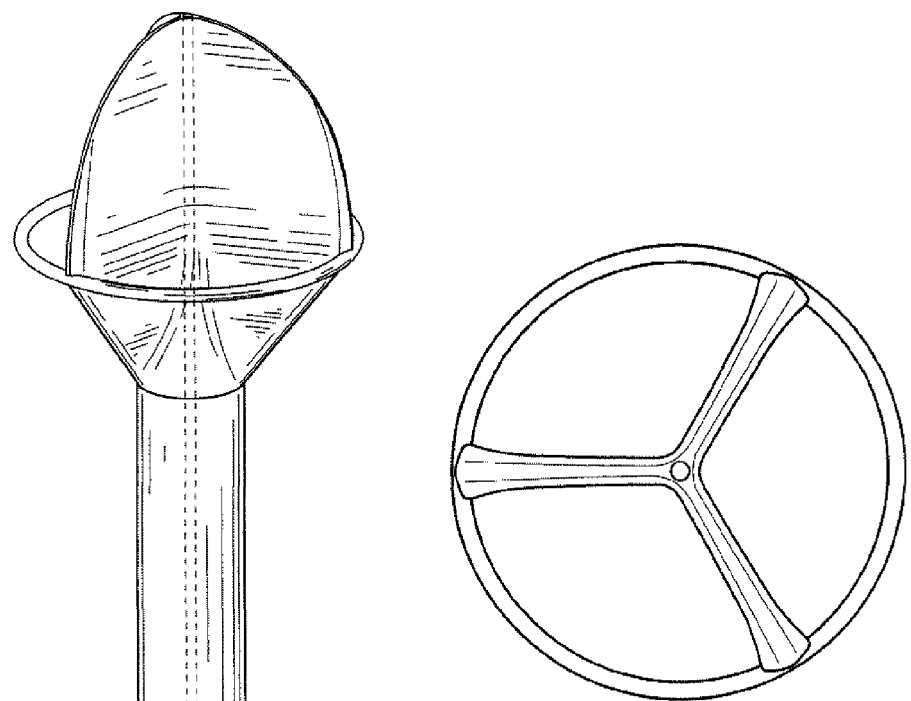

Additionally, the top of FIG. 1 of file FIG. 27 (the buttresses) can be nicely rounded like in the example of FIG. 28. It will be appreciated that purse-string or other attachments means can be used to hold the rod in the apex. This can be with or without soft silicon ring as demonstrated in 6. FIGS. 25, 26, 27 demonstrate examples of a rod that can be utilized for the buttress for the mitral position before it has been covered with pericardium and the ring has been added. It will be introduced through the same rod like FIG. 17 and 18 the above-incorporated U.S. patent application Ser. No. 12/886,087, but instead of injecting in the mitral position, it will be introduced a little more than is shown therein, such that the device can be implanted to a position—with or without the ring. Again, if a ring is used, the ring will be below the cusp in the ventricle, contrary to the mitral buttress ring, which sits in the left atrium (the ring is always in the inflow of the valve).

Figure 29:
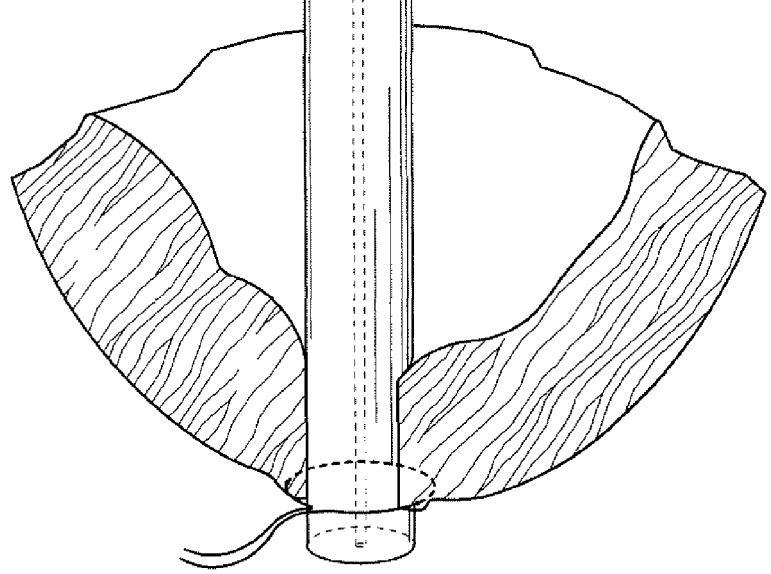

In the example of the apparatus depicted in FIG. 29 the buttress comprises a plurality of buttress portions that extend radially from a central axial region of the buttress. Each of the buttress portions extend axially from a proximal end and terminate at a distal end thereof. The elongated rod extends from the distal end of the buttress. Each pair of adjacent buttress portions provides a continuous contact surface that is dimensioned and configured to be engaged by a respective leaflet of a heart valve when the apparatus is implanted in the heart valve. The buttress permits flow of blood adjacent to each contact surface of the buttress.

Another aspect can be to determine an appropriate size (diameter) of the prosthesis that is to be implanted. This can be done prior implanting the prosthesis disclosed herein. The sizing method as well as the implantation of the prosthesis can be performed in the absence of cardiopulmonary bypass. A plurality of differently sized sizing apparatuses (e.g., ranging from 10 mm to about 40 mm) and having the same configuration as the prosthesis can be utilized during as part of a sizing method to determine the correct size for the prosthesis. The sizing apparatus can include an elongated rod that extends outwardly from the device (e.g., from a central or annular location). The rod should be sufficiently long to extend from the annulus through the apex and to a position that is external to the heart. The external length should further be sufficient to allow a user to grip it and adjust its position. The entire sizing apparatus can be made of a flexible material, such as a silicon or surgical rubber material, and can be formed as a monolithic structure. The rod also should be sufficiently rigid to be able to adjust the position of the apparatus axially and rotationally during sizing. Additionally, the rod of the sizing apparatus can have an axially extending lumen in the middle of it (e.g., a 2-3 mm diameter lumen). This lumen can be configured as to provide a path to allow guide wire and/or a catheter to reach the left atrium to confirm the position of the device.

By way of example, the sizing method can include:
1. Creating an aperture in the apex (e.g., via scalpel or a coring device)—The aperture can be formed through a center of purse string suture that has been applied at the apex. As disclosed herein the purse string can be used to selectively open and close he aperture during the sizing.
2. Inserting a trocar or similar device through the aperture—The trocar can include a lumnen that is insertable through the aperture and into the heart. Such trocar can be used as a portal to insert the sizing apparatus.
3. Selecting a sizing apparatus—A sizing apparatus can be selected based on a surgeon's expected (or known) size, such as may be decided from 2D echocardiogram or other imaging technique. The sizing apparatus can be deformable to a reduced cross-sectional dimension to enable its insertion into and through the trocar.
4. A sizing apparatus can be deformed to a reduced cross sectional dimension sufficient to be inserted into the trocar. The sizing apparatus can then be advanced through the trocar into the heart chamber and positioned at the valve annulus (e.g., the mitral valve annulus). The sizing apparatus can be rotated so that the buttress thereof is aligned for coaptation with the patient's healthy leaflet(s). The purse string suture can be used to temporarily close the aperture (with or without the trocar within the heart).
5. Determining if the size is correct—With the apical opening closed, an appropriate vision system (2D echo) can be utlized to determine if a particular configuration of the contact member provides effective coaptation with any viable leaflets in the valve. The point where effective coaptation takes place can be determined by the surgeon using the vision system. The sizing apparatus can then be withdrawn back through the trocar. If the size is determined to provide for only trivial regurgitation or no regurgitation was observed, the correct size prosthesis is known and can be implanted as disclosed herein. If the size is not correct, it may be withdrawn and the sizing repeated by inserting a larger or smaller sizing apparatus. This process can be repeated until the correct size is determined.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. An apparatus for mitigating prolapse comprising
   a support member having a flexible buttress, the support member configured to position the buttress spaced apart from at least one viable leaflet of a patient's own heart valve, the buttress configured to coapt with the at least one viable leaflet to provide for unidirectional flow of blood in the space between the buttress and the at least one viable leaflet;
   an elongated tubular rod attached to and extending generally axially from the buttress and being dimensioned and configured with a length sufficient to extend from the annulus and anchor in tissue axially displaced from a valve annulus associated with the patient's heart valve, the support member and the elongated tubular rod forming a unitary structure, the elongated tubular rod being configured to stabilize the support member and buttress at a desired axial position and angular orientation relative to the patient's heart valve annulus; and
   a lumen extending axially through the elongated tubular rod and through the support member.

2. The apparatus of claim 1, wherein the tissue is located at or adjacent the apex of the heart.

3. The apparatus of claim 1, wherein the support member further comprises a flexible annular structure configured to be deformable between a reduced and expanded cross-sectional dimension, the annular structure being dimensioned and configured in the expanded cross-sectional dimension to engage the valve annulus and to maintain a position of the buttress to facilitate coaptation of the at least one viable leaflet with the buttress.

4. The apparatus of claim 3, wherein the annular structure comprises a substrate of a compliant material covered with a substantially biocompatible layer of biological material.

5. The apparatus of claim 3, wherein the buttress further comprises a pair of opposing contact surfaces configured to engage opposing leaflets, the opposing contact surfaces of the buttress being connected between opposed sides of the annular structure and extending axially from the annular structure to terminate in a distal end thereof, the elongated tubular rod extending axially from the distal end of the buttress.

6. The apparatus of claim 1, Wherein the buttress further comprises a plurality of buttress portions extending radially from a central axial region of the buttress, each of the buttress portions extending axially from a proximal end to terminate in a distal end thereof, the elongated tubular rod extending from the distal end of the buttress,
   each pair of adjacent buttress portion providing a continuous contact surface dimensioned and configured to be engaged by a respective leaflet of the heart valve when the apparatus is implanted in the heart valve, whereby the buttress permits flow of blood adjacent each contact surface of the buttress.

7. The apparatus of claim 1, wherein the support member further comprises:
   a generally arcuate base portion,
   the buttress being farther configured to extend radially inwardly and axially relative to the base portion so as to permit substantially bi-directional flow of blood axially relative to the apparatus, a contact surface of the buttress having a surface dimensioned and configured to be engaged by at least one leaflet of the heart valve when the apparatus is implanted at the heart valve, whereby when the apparatus is implanted at the heart valve, movement of the at least one leaflet of the heart valve relative to the surface of the buttress provides substantially unidirectional flow of blood relative to the apparatus.

8. The apparatus of claim 7, Wherein the elongated tubular rod extends from a distal end of the buttress that is spaced from the base portion.

9. The apparatus of claim 3, wherein the annular structure comprises a substrate of a compliant material covered with a layer of synthetic biocompatible material.

10. An apparatus for mitigating prolapse comprising:
    a support member covered with a substantially biocompatible layer of biological material, the support member having a flexible buttress, the support member configured to position the buttress spaced apart from at least one viable leaflet of a patient's own heart valve, the buttress configured to coapt with the at least one viable leaflet to provide for unidirectional flow of blood in the space between the buttress and the at least one viable leaflet;
    an elongated tubular rod covered with a substantially biocompatible layer of biological material, the elongated tubular rod being attached to and extending generally axially from the buttress and being dimensioned and configured with a length sufficient to extend from the annulus and anchor in tissue axially displaced from a valve annulus associated with the patient's heart valve, such that when implanted the elongated tubular rod can stabilize the support member and buttress at a desired axial position and angular orientation relative to the patient's heart valve annulus; and
    a lumen extending axially through the elongated road and through the support member.

11. The apparatus of claim 1 further comprising a guidewire extending through the lumen, the guidewire being dimensioned and configured to permit relative movement between the unitary structure and the guidewire.

12. The apparatus of claim 10, further comprising a guidewire extending through and axially moveable with respect to the lumen.

13. An apparatus for mitigating prolapsed comprising:
    a support member having a flexible buttress, the support member configured to position the buttress spaced apart from at least one viable leaflet of a patient's own heart valve, the buttress configured to coapt with the at least one viable leaflet to provide for unidirectional flow of blood in the space between the buttress and the at least one viable leaflet;
    an elongated tubular rod attached to and extending generally axially from the buttress and being dimensioned and configured with a length sufficient to extend from the annulus and anchor in tissue axially displaced from a valve annulus associated with the patient's heart valve, the elongated tubular rod being configured to stabilize the support member and buttress at a desired axial position and angular orientation relative to the patient's heart valve annulus;
    a lumen extending axially through the elongated tubular rod and through the support member; and
    a guidewire extending axially through and moveable with respect to the lumen.

14. The apparatus of claim 13, wherein the support member further comprises a flexible annular structure configured to be deformable between a reduced and expanded cross-sectional dimension, the annular structure being dimensioned and configured in the expanded cross-sectional dimension to engage the valve annulus and to maintain a position of the buttress to facilitate coaptation of the at least one viable leaflet with the buttress.

15. The apparatus of claim 13, wherein the buttress further comprises a plurality of buttress portions extending radially from a central axial region of the buttress, each of the buttress portions extending axially from a proximal end to terminate in a distal end thereof, the elongated tubular rod extending from the distal end of the buttress, each pair of adjacent buttress portions providing a continuous contact surface dimensioned and configured to be engaged by a respective leaflet of the heart valve when the apparatus is implanted in the heart valve, whereby the buttress permits flow of blood adjacent each contact surface of the buttress.

16. The apparatus of claim 13, wherein the support member further comprises:

a generally arcuate base portion, the buttress being further configured to extend radially inwardly and axially relative to the base portion so as to permit substantially bi-directional flow of blood in the space axially relative to the apparatus, a contact surface of the buttress having a surface dimensioned and configured to be engaged by at least one leaflet of the heart valve when the apparatus is implanted at the heart valve, whereby when the apparatus is implanted at the heart valve, movement of the at least one leaflet of the heart valve relative to the surface of the buttress provides substantially unidirectional flow of blood relative to the apparatus.

17. The apparatus of claim 16, wherein the elongated rod extends from a distal end of the buttress that is spaced from the base portion.

\* \* \* \* \*